US005736120A

United States Patent [19]

Srinivasan

[11] Patent Number: 5,736,120
[45] Date of Patent: *Apr. 7, 1998

[54] METHOD FOR PREPARING RADIOLABELED PEPTIDES

[76] Inventor: Ananthachari Srinivasan, 332 Woodmere Dr., St. Charles, Mo. 63304

[*] Notice: The term of this patent shall not extend beyond the expiration date of Pat. No. 5,618,513.

[21] Appl. No.: 660,262

[22] Filed: Jun. 7, 1996

[51] Int. Cl.$^6$ .......................... A61K 51/00; A61M 36/14
[52] U.S. Cl. .......................... 424/1.69; 424/1.65; 534/10; 534/14; 530/300; 530/328
[58] Field of Search .................. 424/1.11, 1.65, 424/1.69; 534/7, 10–16; 530/300, 317, 324–330, 333, 334, 338

[56] References Cited

U.S. PATENT DOCUMENTS

| | | | |
|---|---|---|---|
| 4,988,496 | 1/1991 | Srinivasan et al. | 424/1.11 |
| 5,075,099 | 12/1991 | Srinivasan et al. | 424/1.11 |
| 5,112,953 | 5/1992 | Gustavson et al. | 530/391.5 |
| 5,248,764 | 9/1993 | Flanagan et al. | 530/324 |
| 5,436,352 | 7/1995 | Srinivasan et al. | 548/542 |
| 5,618,513 | 4/1997 | Srinivasan | 424/1.69 |

OTHER PUBLICATIONS

Sluka et al (1990), J. Am. Chem. Soc., vol. 112, No. 17, pp. 6369–6374 "Reagents and Methods for the Solid Phase Synthesis of Protein–EDTA for use in Affinity Cleaving".

Williams et al (1993), J. Org. Chem, vol. 58, No. 5, pp. 1151–1158 "Synthesis of Enantiomerically Pure Diethylenetriaminepentaacetic Acid Analogues".

Williams et al (1994) J. Org. Chem. vol. 59, No. 13, pp. 3616–3625 "Synthesis of Conformationally Constrained DTPA Analogues".

*Primary Examiner*—John Kight
*Assistant Examiner*—Dameron Jones
*Attorney, Agent, or Firm*—Wendell Ray Guffey; Thomas P. McBride

[57] ABSTRACT

A method for radiolabelling peptides using polyaminocarboxylate ligands having suitable protecting groups such that they can be added to peptides by standard solid phase or solution phase peptide synthetic chemistry and can be deproteced using standard cleavage/deprotection reagents and produce the peptide/chelate conjugate as a high purity monoaddition product is provided. The cleaved and deprotected ligand-peptide molecules can then be labeled with lanthanide or actinide radionuclides. The protected polyaminocarboxylate ligands form mono-anhydrides or monoactive esters under solid phase or solution phase conditions and permit only the desired monoaddition chelate-peptide conjugate to be formed.

5 Claims, No Drawings

METHOD FOR PREPARING RADIOLABELED PEPTIDES

FIELD OF THE INVENTION

This invention relates in general to radiolabeled peptides and, more particularly, to the use of polyaminocarboxylate ligands prepared with suitable protecting groups to specifically yield mono substituted derivatives of peptides and peptidomimetics, which then can be labeled with a desired radionuclide.

BACKGROUND OF THE INVENTION

The ability to use radiolabeled peptides or peptidomimetics as diagnostic or therapeutic medical tools has long been a goal of the pharmaceutical industry. This goal is being realized as radiolabeled peptide products have now been introduced into the marketplace. For example, an Indium-111 labeled pentatreotide product has been introduced for somatostatin receptor imaging for neuroendocrine tumors (Mallincrodt Medical, Inc.). As this type of product line matures it will become increasingly important to be able to prepare the radiolabeled peptide product in an efficient, cost-effective manner and in high purity.

The labelling of the peptide with the radionuclide has been one of the primary difficulties in bringing a radiolabeled peptide to the market. It is important that the radionuclide be stably coupled to the peptide when administered in vivo while also not interfering with the biological activity of the peptide. Labelling the peptide directly with a radionuclide is not acceptable because of the possibility that the radionuclide could attach at an important biological site on the peptide and interfere with its activity or specificity. As an alternative to direct labelling, the use of a "bifunctional chelate" in which a composition having a strong chelating group capable of covalently bonding to the peptide and being labelled with the radionuclide has been proposed. One such approach is described in U.S. Pat. No. 4,479,930 which issued to D. J. Hnatowich. In the Hnatowich patent, the method for radiolabelling peptides involves the reaction of a peptide with a dicyclic anhydride of a defined formula (generally a DTPA-type or EDTA-type compound) and then adding a radionuclide to the peptide/chelate conjugate. Even though useful in the radiolabelling of a peptide, the method described in Hnatowich has one significant drawback; it is not capable of specifically coupling only one peptide per chelate and, in practice, the resulting peptide/chelate conjugate is predominantly formed as a diaddition product. The diaddition product is not clinically useful and must be removed by lengthy, complicated and costly purification processes. Furthermore, valuable peptide is lost in this process. This problem is further illustrated in Example 1 of PCT International Publication Number WO 90/06949.

Most prior attempts at radiolabelling peptides have used standard organic chemistry procedures to couple the chelating group to a previously prepared peptide. It would be advantageous if the chelating group could be incorporated into the peptide as the peptide is being formed using solid phase peptide synthetic chemistry. Kazmierski [Tet. Letters, 4493 (1993); and Int.J. Peptide and Protein Res., 45, 241–247 (1995)] was concerned with synthesizing metal binding peptides incorporating aminodiacetic acid based ligands, but suggested that prederivitized amino acids containing the ligand be prepared and the peptides incorporated during peptide synthesis. Moreover, Kazmierski requires that one of the bonding atoms for the metal come from the nitrogen group of the amino acid which could adversely affect the biological activity of the peptide. This significantly limits the usefulness of this approach. Sluka, et al. [J. Amer. Chem. Soc., 112, 6369 (1990)] described a method for the solid-phase synthesis of protein-EDTA for use in affinity cleaving, but this method was not adapted for use with polyaminocarboxylic acids nor for binding the medically useful lanthanide and actinide radionuclides. W. B. Edwards, et al. [J. Med. Chem., 37, 3749 (1994)] discolsed the coupling of DTPA-bis-anhydride to the N-terminal D-Phe of the heptapeptide attached to HMP-resin followed by aminolysis to generate the mono DTPA derivative in 5% yield. The low yield can be attributed to formation of the diaddition DTPA-(peptide)$_2$ derivative.

There is, therefore, a need for a method for radiolabelling peptides utilizing polyaminocarboxylate ligands of the DTPA or EDTA type in a solid phase peptide synthesis process in which no undesirable diaddition products are formed and only the desired monoaddition product is formed in high purity.

SUMMARY OF THE INVENTION

The present invention is directed to a method for making a radiolabeled peptide using polyaminocarboxylate ligands formulated with suitable protecting groups such that they can be added to peptides by standard solid phase or solution phase peptide synthetic chemistry and can be deprotected using standard cleavage/deprotection reagents in a manner forming only the monoaddition product and not the undesired diaddition product. The cleaved and deprotected ligand-peptide molecules can then be labeled with lanthanide or actinide radionuclides. The protected polyaminocarboxylate ligands form mono-anhydrides or mono-active esters under solid phase or solution phase conditions and permit only the desired monoaddition chelate-peptide conjugate to be formed.

The present invention is further directed to a method for preparing a chelate for use in attaching a radionuclide to a peptide such that only the monoaddition chelate/peptide conjugate is formed and a method of using such a chelate in the process of making a radiolabeled peptide.

Among the many advantages of the present invention include the provision of a method for radiolabelling a peptide using solid phase synthetic peptide chemistry that permits the introduction of the radiolabel at any location in the peptide; the provision of such a method that does not require the prederivitization of individual amino acids; the provision of such a method that can be used to bind medically useful radionuclides such as lanthanides and actinides; and the provision of such a method that provides only the desired monoaddition peptide/chelate conjugate in high purity.

DESCRIPTION OF THE PREFERRED EMBODIMENTS

In accordance with the present invention, it has been discovered that a bifunctional chelating agent capable of binding a radionuclide can be coupled to a peptide, peptidomimetic or the like in a solid phase peptide synthesizer in a manner that yields only the desired monoaddition peptide/chelate conjugate in high purity. In this method, the undesired diaddition peptide/chelate conjugate produced by prior art methods is not formed and the need for complicated and tedious purification and isolation procedures is eliminated.

The bifunctional chelating agents useful in connection with this invention are polyaminocarboxylate ligands having the general formula below:

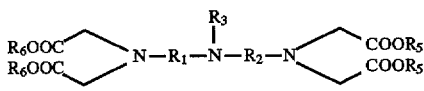

where $R_1$ and $R_2$ are same or different and are linking moieties containing between about 1 and about 10 carbon atoms;

$R_3$ is a hydrogen, alkyl group having 1–15 carbon atoms such as methyl, ethyl, propyl, butyl, pentyl, isopropyl, isobutyl, or a branched or straight chain carboxyalkyl group of the formula:

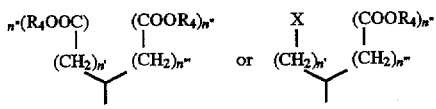

where X is one of $NH_2$, NCS, NCO, OH, SH, $C_6H_4$—$NH_2$, $C_6H_4$—NCS, $C_6H_4$—NCO, $C_6H_4$—OH $C_6H_4$—SH; n' is 0–5; n" is 0, 1 or 2; and n'" is 0–5; $R_4$–$R_6$ are hydrogen or a protecting group; and wherein only one of $R_4$, $R_5$ or $R_6$ is hydrogen; or

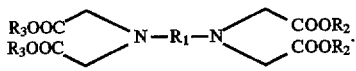

where $R_1$ is a linking moiety containing between 1 and 20 carbon atoms; $R_2$ and $R_3$ are hydrogen or a protecting group; and wherein only one of $R_2$ or $R_3$ s hydrogen.

These ligands are prepared with suitable protective groups such that they provide only one active site to which the ligand may bind to a single peptide and such that it can be added to a peptide utilizing standard solid phase peptide synthetic chemistry and deprotected using standard cleavage/deprotection reagents. Suitable protective groups inlude but are not limited to t-butyl, benzyl, methyl- or methoxy-substituted benzyl, trityl, and any other group that is compatible with the synthetic chemistry and amenable to removal under cleavage/deprotection conditions. As is well understood by those knowledgeable in solid phase peptide synthesis chemistry, various combinations of solid phase resins and protective groups can be selected so that the prepared compound could be cleaved intact, cleaved with selective deprotection, or cleaved and completely deprotected depending on the specific situation. The ligand can be prepared so that it is incorporated at the amino terminus, carboxy terminus, or the interior of the peptide by modifying the chelating agent. Preferred ligands include those identified as Compound 1 and Compound 2 in Table 1 hereinbelow.

Any peptide can be bound to the polyaminocarboxylate chelating groups described above. As used herein, the terms "peptide" or "peptidomimetic" means a compound of two or more amino acids, or amino acid analogues. Examples of suitable peptides are polypeptides having immunological or receptor binding activity such as antibodies, antibody fragments, protein receptors. Peptides or a polypeptide having targeting capabilities includes any molecule that can bind to a defined population of cells. Antibodies include both polyclonal and monoclonal antibodies, and may be intact molecules, fragments or a functional equivalent, or may be genetically engineered. Antibody fragments include $F(ab')_2$, Fab', Fab, and Fv. Exemplary peptides include adrenocorticotropic hormone, atrial natriurtic peptides, bradikinins, chemotactic peptides, dynorphin, fibronectin fragments, growth hormone releasing peptides, LHRH, SMS, Substance P and related peptides.

Any radionuclide having diagnostic or therapeutic value can be used as the radiolabel. In a preferred embodiment, the radionuclide is a γ-emitting or β-emitting radionuclide selected from the lanthanide or actinide series of the elements. Positron-emitting radionuclides, e.g. 68Ga or 64Cu, may also be used.

Suitable γ-emitting radionuclides include those which are useful in diagnostic imaging applications. The γ-emitting radionuclides preferably have a half-life of from 1 hour to 40 days, preferably from 12 hours to 3 days. Examples of suitable γ-emitting radionuclides include 67Ga, 111In, 99mTc, 169Yb and 186Re. Most preferably, the radionuclide is 99mTc.

Suitable β-emitting radionuclides include those which are useful in therapeutic applications. Examples include 90Y, 67Cu, 186Re, 188Re, 169Er, 121Sn, 127Te, 143Pr, 198Au, 109Pd, 165Dy, 32P, 142Pr, and 153Sm. The β-emitting radionuclide preferably has a half-life of from 2 hours to two weeks, and more preferably from about 2 hours to 100 hours.

The peptide/chelate conjugates of the invention are labeled by reacting the conjugate with the selected radionuclide, e.g. a metal salt, preferably water soluble. The reaction is carried out by known methods in the art preferably using a reducing agent (e.g., stannous chloride) and a transfer agent (e.g., tartrate, gluconate, citrate or mannitol) and a heating step, when necessary.

The radiolabeled peptide/chelate conjugates of the invention and their pharmaceutically acceptable salts are useful as a diagnostic imaging agent or in therapeutic applications. The radiolabeled peptide/chelate conjugate is prepared in a pharmaceutically acceptable carrier, e.g. saline or blood plasma, and is administered to an individual in a diagnostically or therapeutically effective amount as determined using standard methods known to those in the art. The carrier may also contain pharmaceutically acceptable adjunct materials such as salts, buffers, preservatives and the like. Preferably, the radiopharmaceutical composition of the present invention is provided in a kit whereby the radionuclide is provided in one vial and the peptide/chelating group conjugate is provided in a second vial and the contents mixed just prior to administration. The mixture may be heated if necessary to effect complete labelling. The provision of such radiolabeled complexes in kit form and the preparation of the final radiolabeled product are standard and routine in the field of nuclear medicine. The final radiopharmaceutical product should be of high radiochemical purity, preferably greater than 95%, and at least greater than 90%, as determined by standard protocols known in the art.

The radiolabeled complex is prepared to provide a radioactive dose of between about 0.05 mCi and about 40 mCi, preferably about 1 mCi to about 20 mCi, to the individual in accordance with standard radiopharmaceutical dosing determinations. As used herein, "a diagnostically effective amount" means an amount of the radiopharmaceutical sufficient to permit its detection by scintigraphic means and "a therapeutically effective amount" means an amount sufficient to effect a therapeutic treatment at the targeted biological site. The radiolabeled peptides may be administered intravenously in any conventional medium for intravenous injection. Imaging of the biological site may be effected within about 2–5 minutes post-injection, but may also take place several hours post-injection. Any conventional method of imaging for diagnostic purposes may be utilized.

The following examples describe preferred embodiments of the invention. Other embodiments within the scope of the claims herein will be apparent to one skilled in the art from consideration of the specification or practice of the invention as disclosed herein. It is intended that the specification, taken together with the examples, be considered exemplary only, with the scope and spirit of the invention being indicated by the claims.

EXAMPLE 1

This example describes the preparation of 1,1,4-Tris(t-butyloxycarbonylmethyl) -7,7-bis(carboxymethyl)-1,4,7-triazaheptane (Compound 1 as shown in Table 1) which is suitable for use as a chelate in connection with the methods of the present invention.

Compounds 1A and 1B (structures shown in Table 1) were prepared according to the procedure of M. A. Williams and H. Rapoport, J. Org. Chem., 58, 1151 (1993).

To prepare Compound 1C (structure in Table 1), a mixture of t-butyl glycinate hydrochloride (60 mmol), diisopropylethyl-amine (125 mmol), 2-[bis-(t-butyloxycarbonyl-methyl)amino] ethyl bromide (Compound 1A, 48 mmol), and 500 ml of acetonitrile was stirred under argon and refluxed for 3 days. The mixture was cooled and the solvent was removed in vacuo. The material was partitioned between methylene chloride and water. The layers were separated and the methylene chloride layer was washed with water and brine. The methylene chloride solution was dried and evaporated. Compound 1C was isolated by column chromatography.

To prepare Compound 1D (structure in Table 1), a mixture of Compound 1C (7.4 mmol), diisopropylethylamine (1.75 ml, 10 mmol), Compound 1B (8.1 mmol), and 60 ml of acetonitrile was stirred and refluxed for 24 hours. The mixture was cooled to room temperature and the solvent was removed in vacuo. The material was partitioned between methylene chloride and water. The layers were separated and the methylene chloride layer was washed with water and brine. The methylene chloride solution was dried and evaporated. Compound 1D was isolated by column chromatography and yielded 4.57 g. To produce Compound 1 (structure in Table 1), a mixture of 10% palladium on carbon (0.66 g) and a solution of Compound 1D (4.4 g, 5.9 mmol) in 200 ml of methanol was hydrogenylized at 50 psi for 4 hours. The mixture was filtered and the solvent was removed in vacuo to yield Compound 1. Purification of Compound 1 was performed by column chromatography.

TABLE 1

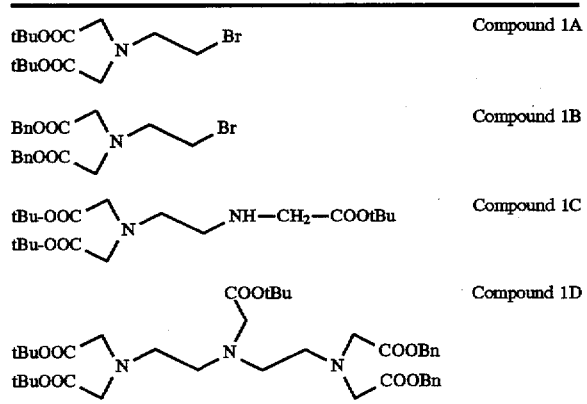

TABLE 1-continued

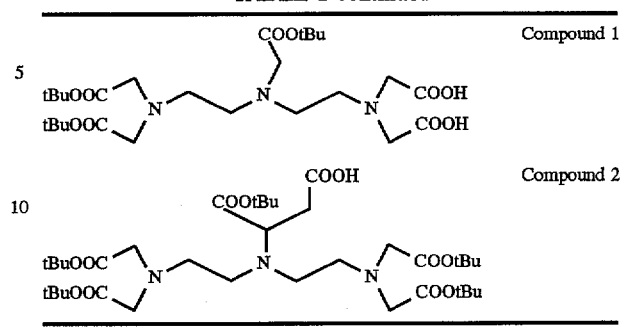

Compound 2

EXAMPLE 2

This example describes the preparation of Compound 2 (structure shown in Table 1) which is suitable for use as a chelate in connection with the method of the present invention.

Compound 2,1,1,7,7-tetra(t-butoxycarbonylmethyl)-4-(1-t-butoxy carbonyl)-2'-(carboxyethyl)-1,4,7-triazaheptane, was prepared according to the general procedure described in Example 1 except that α-t-butyl-β-benzyl aspartic acid was substituted for t-butyl glycinate in the first synthesis step.

EXAMPLE 3

This example describes the preparation of a mono-addition DTPA-Arg$^1$ Substance P peptide/chelate conjugate according to the methods of the invention.

The DTPA-Arg$^1$ Substance P peptide/chelate conjugate was prepared by solid phase peptide synthesis using pre-loaded Fmoc-Met-Rink amide resin on a 0.2–0.3 mmole scale using an Applied Biosystems Model 431 A Peptide synthesizer. 9-fluorenemethoxycarbonyl (Fmoc) protected amino acids were used in the solid phase peptide synthesis. Coupling was carried out with dicyclohexylcarbodiimide/hydroxybenzotriazole using Rink amide resin for C-terminus amides. After the synthesis was completed, the product was cleaved using a solution comprised of trifluoroacetic acid:water:anisole:triisopropylsilane for 1–6 hours at room temperature. The product was precipitated by ether and purified by C-18 reverse phase chromatography. Fmoc deprotection was conducted according to the protocol of the synthesizer.

A cartridge containing one mmole of compound 1 was introduced in the synthesizer for coupling to the peptide chain after the N-terminal Arg coupling was completed. The cleavage and deprotection was carried out as described above to give mono-DTPA-Arg$^1$ Substance P (DTPA-Arg-Pro-Lys-Pro-Gln-Gln-Phe-Phe-Gly-Leu-Met-NH$_2$, m/e 1724 (M+1)) after reverse phase chromatography. The bis addition product was not detected.

EXAMPLE 4

This example describes the preparation of a mono-addition DTPA-Lys$^1$ Substance P (DTPA-Lys-Pro-Lys-Pro-Gln-Gln-Phe-Phe-Gly-Leu-Met-NH$_2$) peptide/chelate conjugate according to the present invention.

This peptide/chelate conjugate was prepared according to the procedure described in Example 3 hereinabove except that Lys[1] Substance P was used as the peptide. The cleavage and deprotection was carried out as described in Example 3 above to give mono-DTPA-Lys[1]-substance P (DTPA-Lys-Pro-Lys-Pro-Gln-Gln-Phe-Phe-Gly-Leu-Met-NH$_2$, m/e 1696 (M+1)) after reverse phase chromatography. The product was isolated in purity ≧99%. Formation of bis addition product was not detected.

EXAMPLE 5

This example describes the preparation of Compound 2-C5a-IP (C5a receptor inhibitory peptide) according to the method of the present invention. The SPS synthesis was carried out using Fmoc-Arg-HMP resin according to the procedure described in Example 3 and 1 mmole of compound 2 was coupled to the peptide chain after the N-terminal Tyr coupling was completed. Mono-Compound 2-C5a-IP (Compound 2-Tyr-Phe-Lys-Ala-Cha-Cha-Leu-D-Ala-Arg-OH) m/e 1609 (M+1)) was isolated after reverse phase chromatography in purity ≧99%.

EXAMPLE 6

Based on the above general method, Fmoc-RC-160 was synthesized using preloaded Fmoc-Thr-Rink amide resin. Cysteines were protected with triphenylmethyl protecting group. Fmoc deprotection was conducted according to the protocol of the synthesizer. A catridge containing one mmol of compound 1 was introduced in the synthesizer for coupling at this stage and the solid phase synthesis was continued according to the general methods. The cleavage and deprotection was carried out as described above to give mono-DTPA-RC-160 (DTPA-D-Phe-Cys-Phe-D-Trp-Lys-Thr-Cys-Thr-NH$_2$, m/e 1509 (M+1) after reverse phase chromatography. Formation of bis addition product was not detected.

EXAMPLE 7

Based on the above general method, a DTPA-Octreotide derivative was synthesized using preloaded Fmoc-Throninol-chlorotritylchloride resin. Cysteines were protected with S-acetamidomethyl protecting group. Fmoc deprotection was conducted according to the protocol of the synthesizer. A catridge containing one mmol of compound 1 was introduced in the synthesizer for coupling at this stage and the solid phase synthesis was continued according to the general methods. The cleavage and deprotection was carried out as described above to give mono-DTPA-bis(S-Acm) Octreotide (DTPA-D-Phe-Cys(Acm)-Phe-D-Trp-Lys-Thr-Cys(Acm)-Thr(OH), m/e 1557 (M+1)) after reverse phase chromatography. Formation of bis addition product was not detected.

What is claimed is:

1. A method for making a radiolabeled peptide composition comprising the steps of:
preparing a chelating agent of the formula:

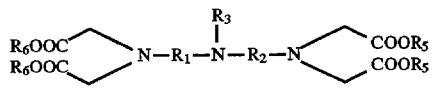

where $R_1$ and $R_2$ are same or different and are linking moieties containing between about 1 and about 10 carbon atoms;
$R_3$ is a hydrogen or a branched or straight chain alkyl-carboxyl group of the formula:

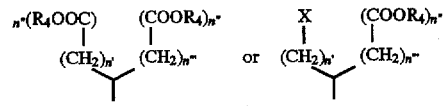

where X is one of NH$_2$, NCS, NCO, OH, SH, C$_6$H$_4$—NH$_2$, C$_6$H$_4$—NCS, C$_6$H$_4$—NCO, C$_6$H$_4$—OH C$_6$H$_4$—SH; n' is 0-5; n" is 0 or 1 and n''' is 0-5;
$R_4$-$R_6$ are hydrogen or a protecting group and wherein only one of $R_4$, $R_5$ or $R_6$ is hydrogen;
combining the chelating agent with a peptide in a solid phase peptide synthesizer to form a chelate-peptide conjugate; and
complexing a radionuclide to the conjugate to form the radiolabeled peptide.

2. The method of claim 1 wherein the chelating agent has the formula:

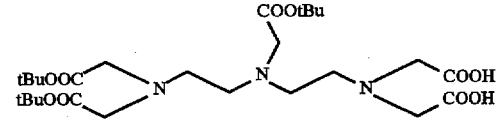

3. The method of claim 1 wherein the chelating agent has the formula:

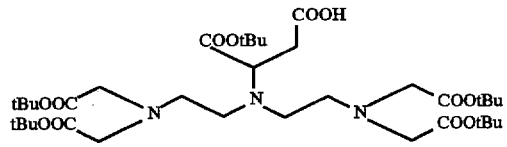

4. The method of claim 1, 2 or 3 wherein the peptide is selected from the group consisting of antibodies, antibody fragments, protein receptors, adrenocorticotropic hormone, atrial natriurtic peptides, bradikinins, chemotactic peptides, dynorphin, fibronectin fragments, growth hormone releasing peptides, Luteinizing Hormone-Releasing Hormone (LHRH), Somatostatin (SMS), and Substance P.

5. The method of claim 4 wherein the radionuclide is selected from the group consisting of 68Ga, 64Cu, 67Ga, 111In, 99mTc, 169Yb, 186Re, 90Y, 67Cu, 186Re, 188Re, 169Er, 121Sn, 127Te, 143Pr, 198Au, 109Pd, 165Dy, 32P, 142Pr, and 153Sm.

* * * * *